United States Patent [19]
Wolsey et al.

[11] Patent Number: 6,067,803
[45] Date of Patent: May 30, 2000

[54] COOLING POUCH

[76] Inventors: Henry Garnet Wolsey; Althea Wolsey, both of Whiteleys, Little Treffgarn, Haverfordwest, Pembrokeshire, SA62 5DY, United Kingdom

[21] Appl. No.: 09/102,340

[22] Filed: Jun. 22, 1998

Related U.S. Application Data

[63] Continuation-in-part of application No. PCT/GB97/02930, Oct. 23, 1997.

[30]     Foreign Application Priority Data

Oct. 23, 1996 [GB]  United Kingdom ................ 9622047
Apr. 4, 1997 [GB]  United Kingdom ................ 9706888

[51] Int. Cl.[7] ....................................................... F25D 3/08
[52] U.S. Cl. ................................. 62/60; 62/457.9; 383/4
[58] Field of Search ........................... 62/60, 315, 457.1, 62/457.9; 206/204; 383/4; 261/100, 101

[56]              References Cited

U.S. PATENT DOCUMENTS

| 3,875,754 | 4/1975 | Faust et al. | 62/60 |
|---|---|---|---|
| 3,893,834 | 7/1975 | Armstrong | 62/4 |
| 4,223,056 | 9/1980 | Di Fronzo | 383/4 |
| 4,619,678 | 10/1986 | Rubin | 62/4 |
| 4,908,248 | 3/1990 | Nakashima et al. | 428/355 |
| 5,031,762 | 7/1991 | Heacox | 62/457.9 |
| 5,353,600 | 10/1994 | Merritt et al. | 62/457.9 |
| 5,413,198 | 5/1995 | Ferris | 383/4 |
| 5,606,746 | 3/1997 | Shelton et al. | 2/102 |
| 5,806,668 | 9/1998 | Bixby | 206/204 |
| 5,865,314 | 2/1999 | Jacober | 62/457.1 |

FOREIGN PATENT DOCUMENTS 8304089   11/1983   WIPO .

*Primary Examiner*—William E. Tapolcai
*Attorney, Agent, or Firm*—Edwin D. Schindler

[57]                ABSTRACT

A portable flexible cooling pouch for cooling and storing vials containing medication. The pouch comprises opposed web members made of a water permeable material which are connected at the edges thereof. At least one of the web members comprises a plurality of compartments which contain a water-absorbent granular material.

57 Claims, 3 Drawing Sheets

COOLING POUCH

This is a continuation-in-part of P.C.T. international Application No. PCT/GB97/02930 (which designates the United States), filed Oct. 23, 1997.

BACKGROUND OF THE INVENTION

The present invention relates to cooling pouches, such pouches being typically for storing medication, such as vials of insulin or the like.

Persons afflicted by diabetes mellitus ("diabetes") are unable to secrete sufficient insulin, which results in excess of sugar in the bloodstream. Sufferers from diabetes may require treatment consisting of hypodermic injections of insulin, as the latter assists the body to metabolize the excess sugar. It is often necessary to store insulin ready for use by injection or the like.

In order to maintain an insulin preparation in a fresh condition, it should be kept at a temperature lower than normal ambient temperature. This requires that the insulin should be stored in a refrigerator or other cooling device, such as, for example, an ice box. However, people suffering from diabetes who require several injections of insulin per day are inconvenienced if they are away from home for a long period of time.

WO83/04089 discloses a portable carrying pouch which contains a removable refrigerating agent, for use when storing insulin. Other portable carrying devices are known for purposes, other than storage of medicines, for example, for carrying food. By way of example, U.S. Pat. No. 4,211,091 discloses a pliable, insulated bag for use as a lunch bag for temporary storage of foodstuffs; U.S. Pat. No. 4,530,220 discloses a deformable bag for use as a cooling medium, which bag comprises an envelope filled with a gel substance, the whole bag being intended to be cooled to a temperature less than $-10°$ C.

Japanese patent application 6178792A discloses a medical insulating appliance having high cooling, antiflammatory and disinfecting effects. Such an appliance is typically used after cooling in a refrigerator. However, such an appliance is designed for cooling a body part and not for transporting and/or cooling medicament.

OBJECTS OF THE INVENTION

It is an object of the present invention to provide a portable cooling pouch which does not require refrigeration.

It is a further object of the invention to provide a pouch for cooling vials and the like, which does not contain removable refrigeration parts.

It is yet a further object of the invention to provide a pouch which can be used as a cooling device even when the user may have no access to a refrigerator, ice box or the like.

SUMMARY OF THE INVENTION

A portable pouch according to the invention, for cooling and storing vials and the like comprises:
(a) a first web member of water permeable material;
(b) a second web member of water permeable material;
(c) hinge means connecting an edge of said first web member, directly or indirectly, to said second web member; and
(d) fastening means for fastening remaining edges of said first web member to remaining edges of said second web member.

At least one of the web members includes a plurality of compartments each containing water-absorbent granular material, the hinge area being free of such compartments.

Typically, each of the web members comprises a plurality of such compartments, each of which contains the water-absorbent granular material.

Preferably each of the web members is of quadrilateral shape, such as rectangular.

The web members are preferably integrally formed with one another from a single web, arranged to be folded along the hinge.

The fastening means typically comprise at least one first element comprising a multiplicity of hooks, and at least one complementary second element comprising a multiplicity of loops engageable with the hooks on the first element. Both the first and second elements are typically in the form of strip or tape.

Preferably, the web members are arranged to be fastened together by the fastening means in such a way that one web member extends beyond the free edge of the other of the web members, so as to form a flap foldable over a marginal portion of the other web member.

Such a flap preferably has fastening means on a first face of the one web member for engagement with complementary fastening means on the marginal portion on the other web member.

According to a first embodiment of the invention, the hinge means connect an edge of the first web member directly to the second web member.

According to a second embodiment of the invention, the hinge means connect an edge of the first web indirectly to the second web member.

In the second embodiment, there is preferably an intervening panel connecting the hinge means to the second web member. In this embodiment, the pouch can, in some arrangements, take the form of a substantially closed box, in which the first web member provides a closure for a tray constituted by the second web, the above-mentioned panel and a plurality of edge panels. However, it is envisaged in this embodiment that the first web member, the second web member, the intervening panel and the edge panels can be formed from a single web.

Preferably, the water permeable material comprises a durable, flexible textile material, such as a woven fabric. A particularly preferred textile material comprises a polyester/cotton fabric blend, although other textile materials such as a nylon or an acrylic may also be used.

Typically, the water-absorbent granular material is one which is capable of regeneration after it has been dried out, preferably over repeated water absorption and desorption cycles. The water-absorbent material preferably comprises a polymeric material, such as an acrylic polymer. Such a polymer may be a cross-linked acrylate or methacrylate polymer, such as a sodium salt thereof.

It is particularly preferred that the water-absorbent granular material is one which has a transition between respective hydrated forms at or close to ambient temperature, such that the latent heat absorbed or evolved on passage through the transition temperature helps to maintain the temperature substantially constant for a prolonged period.

The compartments containing the water-absorbent material may be formed by sewing an elongate double skinned web member in sewing lines extending along the length of the web member; a plurality of such sewing lines is preferably employed so as to divide the web members lengthwise into a plurality of the compartments.

At least one further sewing line is preferably provided transverse to the sewing lines mentioned above so as to control the distribution of the water-absorbent material along the length of the respective compartment or compartments. It is preferred that the further sewing line is provided along the hinge means.

Preferably, the pouch is flexible.

The present invention further comprises a method of storing a closed container of medicine (preferably a vial or the like) which comprises treating the web members of a pouch as described above with cold water, either before or after shaping the web members to form the pouch, so as to cause swelling of the water-absorbent material within the compartments thereof, and disposing the container within the pouch while the compartments contain the swollen water-absorbent material.

BRIEF DESCRIPTION OF THE DRAWINGS

The invention will now be described, by way of example only, with reference to the accompanying drawings, in which.

DETAILED DESCRIPTION OF THE PREFERRED EMBODIMENTS

Figure 1:
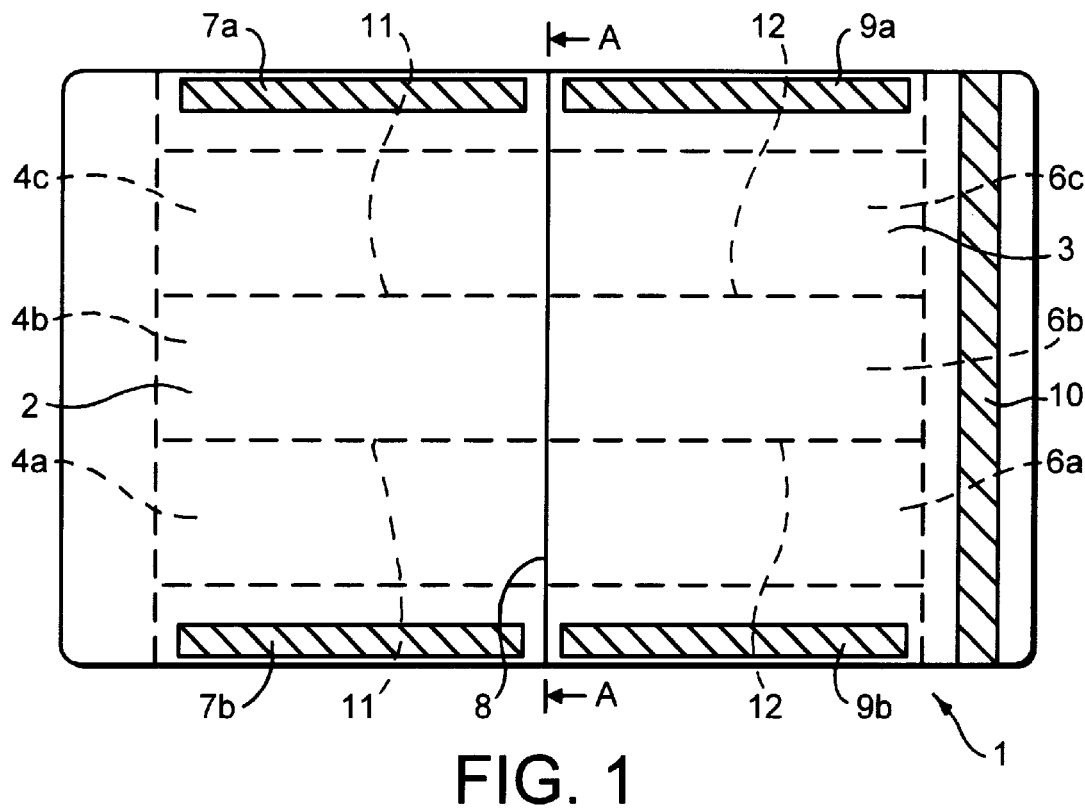
FIG. 1 is a plan view of a first embodiment of the pouch.

Referring to the drawings (and initially to FIGS. 1 and 2), a fabric web 1 includes a double-skinned front fabric panel 2 and a corresponding double-skinned rear fabric panel 3. The front panel 2 has a series of parallel, longitudinally extending stitching lines 11, which (with the corresponding edges of the respective panel) form respective compartments 4a, 4b and 4c, each of which contains water-absorbent grains 5 of sodium polyacrylate (see FIG. 2).

The rear panel 3 also has a series of parallel, longitudinally extending stitching lines 12, which (with the corresponding edges of the respective panel) form respective compartments 6a, 6b and 6c. A strip 7a of one part of a hook-and-loop type fastener of the type commercially available under the trade mark Velcro is sewn to a side edge of the front panel 2; a complementary part of the fastener 9a is sewn to a side edge of the rear panel 3.

A further strip 7b of one part of such a hook-and-loop type fastener is sewn to the opposed side edge of the front panel 2; a complementary part of the fastener 9b is sewn to the corresponding side edge of rear panel 3.

A further strip 10 of one part of such a hook-and-loop type fastener is sewn to the free end of the front panel 2; a complementary part of the fastener (not shown) is sewn to a corresponding end of rear panel 3 (on the obverse face thereof). The free end of the front panel 2 to which strip 10 is sewn thereby forms a flap, which can overlap the corresponding free end of rear panel 3.

A foldline 8 is provided between the front panel 2 and the rear panel 3. This foldline is preferably defined by a row of stitching which separates compartment 4a from 6a, compartment 4b from 6b, compartment 4c from 6c, and compartment 4d from 6d.

The front and rear panels 2,3 are folded together about the foldline and secured together by the various fastening means to form a pouch.

The whole web may be immersed in cold water, typically for about 90 seconds; the grains 5 then form a gel-like substance which can retain the temperature of the water for approximately 3 to 4 days. By taking advantage of evaporative cooling, the contents of the pouch may be at an even lower temperature than the initial temperature of the water. If a temperature significantly lower than that of the cold water is required, it is possible to even further cool the web by placing the whole web in a refrigerator, or the like.

Once the web is at the desired temperature, it is folded along the foldline 8, in order that the front panel 2 can be fastened to the rear panel 3 by means of the fastener 7a,7b, 9a,9b so as to form a pouch. Insulin or other medication that needs to be stored at a lower temperature than room temperature, can then be stored in the pouch, typically in vials or the like, for a period of typically 3 to 4 days.

Figure 3:
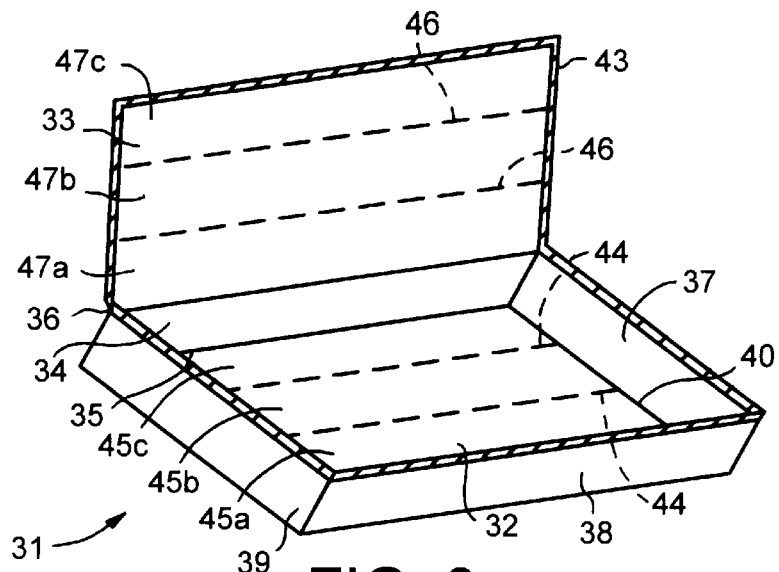
FIG. 3 is a plan view of a second embodiment of the pouch.

Referring to FIG. 3, a fabric webbed box-like pouch 31 comprises a double skinned bottom fabric panel 32 and a corresponding double skinned top fabric panel 33. The bottom panel 32 is attached to the top panel 33 indirectly by hinge panel 34. Hinge panel 34 is attached to the bottom panel 32 along stitching line 35; hinge panel 34 is also attached to the top panel 33 along stitching line 36.

Three further upstanding wall panels 37, 38 and 39 are attached to the bottom panel 32 along respective stitching lines 40, 41 and 42 to form a box-like structure. The top panel 33 can be attached to the upstanding wall panels 37, 38 and 39 by zip fastening 43.

The bottom panel 32 has a series of parallel, longitudinally extending stitching lines 44, which (with the corresponding edges of the respective panel) form respective compartments 45a, 45b and 45c, each of which contains water-absorbent grains 5 of sodium polyacrylate (corresponding to those described above with reference to FIG. 2).

The top panel 33 also has a series of parallel, longitudinally extending stitching lines 46, which (with the corresponding edges of the respective panel) form respective compartments 47a, 47b and 47c.

The whole pouch may be immersed in cold water, typically for about 90 seconds, as described above with reference to the web of FIG. 1.

Figure 4:
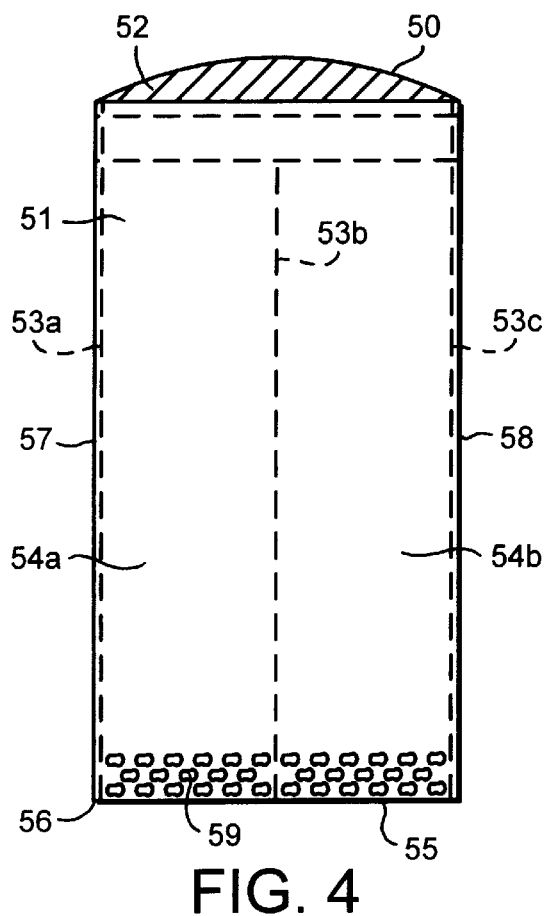
FIG. 4 is a plan view of a third embodiment of the pouch.

Referring to FIG. 4, a fabric web 50 comprises a double-skinned front fabric panel 51 and a corresponding double-skinned rear fabric panel 52. The front panel 51 has three parallel, longitudinally extending stitching lines 53a,53b and 53c, which form respective compartments 54a and 54b, each of which contains water-absorbent grains of sodium polyacrylate 59.

The fabric web 50 further comprises a further stitchline 55 transverse to stitchlines 53, substantially halfway along the length of stitchlines 53, to form a center foldline 56.

The web 50 is thereby folded along foldline 56 and the edges 57 and 58 are secured together (either by a permanent stitchline (not shown), or by hook-and-loop type fastener of the type commercially available under the trade mark VELCRO (not shown)).

Figure 5:
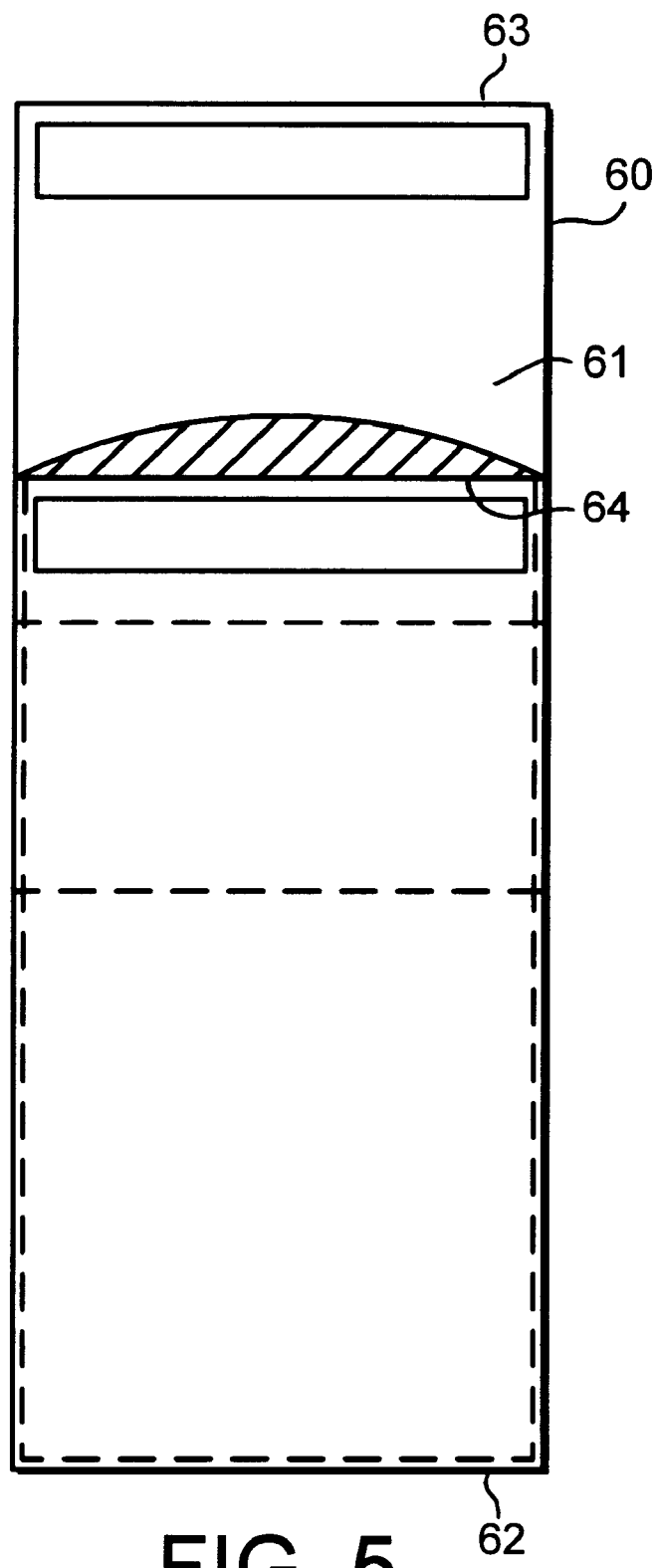
FIG. 5 is a plan view of a carrier which may be used with a cooling pouch according to the present invention.

Referring to FIG. 5, a carrying pocket or sachet 60 is provided to carry a cooling pouch according to the present invention.

An elongate fabric web member 61, typically of a fabric which has breathable and high absorption characteristics, such as the fabric known under the trade mark CAMBRELLE, is folded about a foldline 62. The foldline 62 is arranged such that the first end 63 of web member 61 extends beyond the second end 64, so as to form a foldable flap which may be attached to a portion of web 61 beyond the second end 64.

A cooling pouch according to the first aspect of the present invention is typically immersed in cold water, thereby allowing the grains of sodium polyacrylate to form a gel-like substance. The outer surface of the cooling pouch is then wiped to remove excess water and placed inside the carrying pocket.

EXAMPLE

Figure 2:
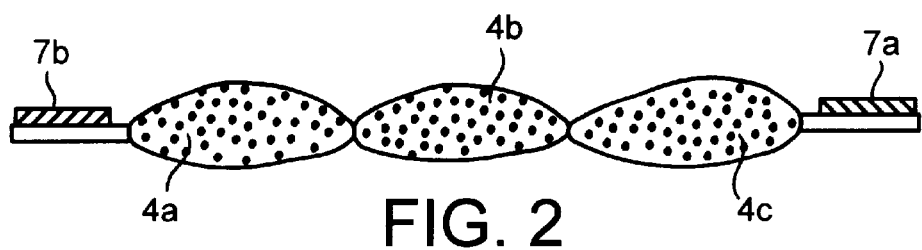
FIG. 2 is a cross-section along the line AA shown in FIG. 1.

Measurements were made of the temperature of the inside of an empty pouch such as that shown in FIG. 1. After immersion of the pouch in cold water, temperature measurements were made of the pouch which was suspended in an incubator where the air temperature was maintained close to 37.8° C. (100° F.) with low relative humidity (15%). Measurements were made at 10 minute intervals for periods of between 24 and 48 hours. The pouch maintained internal temperatures below 30° C. for periods exceeding 14 hours.

We claim:

1. A portable pouch for cooling and storing vials and the like, said pouch comprising:
   (a) a first web member of water permeable material;
   (b) a second web member of water permeable material;
   (c) hinge means connecting an edge of said first web member, directly or indirectly, to said second web member;
   (d) fastening means for fastening remaining edges of said first web member to said second web member, wherein at least one of said web members includes a plurality of compartments each containing water-absorbent granular material and said hinge means is free of such compartments.

2. A pouch according to claim 1, wherein each of said web members comprises a plurality of said compartments.

3. A pouch according to claim 1, wherein each of said web members is of a quadrilateral shape.

4. A pouch according to claim 1, wherein each of said web members is integrally formed from a single web, arranged to be folded along said hinge means.

5. A pouch according to claim 1, wherein said fastening means comprise at least one first element comprising a multiplicity of hooks, and at least one complementary second element comprising a multiplicity of loops engageable with said hooks.

6. A pouch according to claim 5, wherein said complementary elements are in the form of strip or tape.

7. A pouch according to claim 1, wherein said web members are arranged to be fastened together by said fastening means in such a way that one end of one said web member extends beyond a free edge of the other of said web members, so as to form a flap foldable over a marginal portion of said other web member.

8. A pouch according to claim 7, wherein said flap has fastening means on a first face of said one web member for engagement with complementary fastening means on the marginal portion on said other web.

9. A pouch according to claim 1, wherein said hinge means are arranged to connect an edge of said first web member directly to said second web member.

10. A pouch according to claim 1, wherein said hinge means are arranged to connect an edge of said first web indirectly to said second web member.

11. A pouch according to claim 10, wherein an intervening panel connects said hinge means to said second web member.

12. A pouch according to claim 10, which is arranged to form a substantially closed box.

13. A pouch according to claim 12, wherein said second web member provides a closure for a tray constituted by said first web member, said intervening panel and a plurality of edge panels.

14. A pouch according to claim 13, wherein said first web member, said second web member, said intervening panel and said edge panels are formed from a single web.

15. A pouch according to claim 1, wherein said edges are along longitudinally extending edges of the respective web members.

16. A pouch according to claim 1, wherein said water permeable material comprises a durable, flexible textile material.

17. A pouch according to claim 16, wherein said textile material comprises a woven fabric.

18. A pouch according to claim 17, wherein said woven fabric comprises a polyester/cotton fabric blend.

19. A pouch according to claim 1, wherein said water-absorbent material is one which is capable of regeneration after it has been dried out.

20. A pouch according to claim 1, wherein said water-absorbent material comprises a polymeric material.

21. A pouch according to claim 20, wherein said polymeric material comprises an acrylic polymer.

22. A pouch according to claim 21, wherein said acrylic polymer comprises a cross-linked acrylate or methacrylate polymer.

23. A pouch according to claim 1, wherein said granular material has a transition between respective hydrated forms at or close to ambient temperature.

24. A pouch according to claim 1, wherein said compartments containing said water-absorbent material are formed by sewing an elongate double skinned web member in sewing lines extending along the length of said web member.

25. A pouch according to claim 24, which includes a plurality of said sewing lines which divide said web members lengthwise into a plurality of said compartments.

26. A pouch according to claim 25, wherein at least one further sewing line is provided transverse to said lengthwise direction.

27. A pouch according to claim 26, wherein said further sewing line is provided along said hinge means.

28. A pouch according to claim 1, which is flexible.

29. A method of storing a closed container of medicine, which comprises providing a pouch according to claim 1, treating the web members thereof with cold water, so as to cause swelling of said water-absorbent material within said compartments, and disposing said container within the pouch while the compartments contain the swollen water-absorbent material.

30. A method according to claim 29, wherein said container is a vial.

31. A pouch according to claim 1, in combination with a sachet shaped and dimensioned to receive said pouch.

32. A combination according to claim 31, wherein said sachet is of a breathable moisture-absorbing fabric.

33. A portable flexible pouch for cooling and storing vials, said pouch comprising:
   (a) a double-skinned textile web member of water permeable material, said web member including a first double-skinned web portion interconnected, directly or indirectly, via a hinge portion at an edge thereof to a second double-skinned web portion; and,
   (b) fastening means for fastening remaining edges of said first web portion to said second portion,
wherein at least one of said web portions includes a plurality of compartments, each of said compartments containing a water-absorbent granular polymeric material capable of alternately absorbing water and desorbing water upon drying out, said polymeric material having a transition between respective hydrated forms at, or close to, ambient temperature, with said hinge portion being free of said compartments containing said polymeric material and defined by a row of stitches, and said plurality of compartments being separated from one another by stitches, said stitches containing respective skins of said double-skinned textile member.

34. The portable flexible pouch for cooling and storing vials according claim 33, wherein said first double-skinned web portion and said second double-skinned web portion each comprise a plurality of said compartments.

35. The portable flexible pouch for cooling and storing vials according claim 33, wherein said first double-skinned web portion and said second double-skinned web portion are each of a quadrilateral shape.

36. The portable flexible pouch for cooling and storing vials according claim 33, wherein said fastening means comprises at least one complementary first element comprising a multiplicity of hooks, and at least one complementary second element comprising a multiplicity of loops engageable with said hooks.

37. The portable flexible pouch for cooling and storing vials according claim 36, wherein said complementary first element and said complementary second element are in the form of a strip of tape.

38. The portable flexible pouch for cooling and storing vials according claim 33, wherein said first double-skinned web portion and said second double-skinned web portion are arranged to be fastened together by said fastening means, so that one end of one of said web portions extends beyond a free edge of the other of said web portions, so as to form a flap foldable over a marginal portion of said other web portion.

39. The portable flexible pouch for cooling and storing vials according claim 38, wherein said flap has fastening means on a first face of said web portion for engagement with complementary fastening means on the marginal portion on said other web portion.

40. The portable flexible pouch for cooling and storing vials according claim 33, wherein said edges are along longitudinally extending edges of respective said first double-skinned web portion and said second double-skinned web portion.

41. The portable flexible pouch for cooling and storing vials according claim 33, wherein said double-skinned textile web member is made of a textile material comprising a woven fabric.

42. The portable flexible pouch for cooling and storing vials according claim 41, wherein said woven fabric comprises a polyester/cotton fabric blend.

43. The portable flexible pouch for cooling and storing vials according claim 33, wherein said polymeric material comprises an acrylic polymer.

44. The portable flexible pouch for cooling and storing vials according claim 43, wherein said acrylic polymer comprises a cross-linked acrylate polymer.

45. The portable flexible pouch for cooling and storing vials according claim 43, wherein said acrylic polymer comprises a cross-linked methacrylate polymer.

46. The portable flexible pouch for cooling and storing vials according claim 33, wherein said plurality of compartments containing said water-absorbent granular polymeric material are formed by sewing an elongate double-skinned web member in sewing lines extending along the length of said web portion.

47. The portable flexible pouch for cooling and storing vials according claim 46, further comprising a plurality of said sewing lines for dividing said first double-skinned web portion and said second double-skinned web portion lengthwise into a plurality of said compartments.

48. The portable flexible pouch for cooling and storing vials according claim 47, wherein at least one further sewing line is provided transverse to said lengthwise direction.

49. The portable flexible pouch for cooling and storing vials according claim 33, wherein said hinge portion connects on edge of said first double-skinned web portion directly to said second double-skinned web portion.

50. The portable flexible pouch for cooling and storing vials according claim 33, wherein said hinge portion connects on edge of said first double-skinned web portion indirectly to said second double-skinned web portion.

51. The portable flexible pouch for cooling and storing vials according claim 50, further comprising an intervening panel connecting said hinge portion to said second double-skinned web portion.

52. The portable flexible pouch for cooling and storing vials according claim 51, wherein said pouch forms a substantially closed box.

53. The portable flexible pouch for cooling and storing vials according claim 52, wherein said second double-skinned web portion provides a closure for a tray constituted by said first double-skinned web portion, said intervening panel and a plurality of edge panels.

54. The portable flexible pouch for cooling and storing vials according claim 53, wherein said first double-skinned web portion, said second double-skinned web portion, said intervening panel and said plurality of edge panels are formed from a single web.

55. The portable flexible pouch for cooling and storing vials according claim 50, wherein said pouch forms a substantially closed box.

56. A method for storing medicine, comprising the steps of:
   treating a first double-skinned web portion and a second double-skinned web portion of a portable flexible pouch, said pouch comprising:
      (a) a double-skinned textile web member of water permeable material, said web member including a first double-skinned web portion interconnected, directly or indirectly, via a hinge portion at an edge thereof to a second double-skinned web portion; and,
      (b) fastening means for fastening remaining edges of said first web portion to said second portion,
   wherein at least one of said web portions includes a plurality of compartments, each of said compartments containing a water-absorbent granular polymeric material capable of alternately absorbing water and desorbing water upon drying out, said polymeric material having a transition between respective hydrated forms at, or close to, ambient temperature, with said hinge portion being free of said compartments containing said polymeric material and defined by a row of stitches, and said plurality of compartments being separated from one another by stitches, said stitches containing respective skins of said double-skinned textile member, with cold water for causing swelling of said water-absorbent granular polymeric material within said plurality of compartments; and,
   disposing said medicine within said pouch while said plurality of compartments contain the swollen water-absorbent granular polymeric material.

57. The method for storing medicine according to claim 56, wherein the medicine is contained within a vial.

* * * * *

(12) EX PARTE REEXAMINATION CERTIFICATE (8850th)
United States Patent
Wolsey et al.

(10) Number: US 6,067,803 C1
(45) Certificate Issued: Feb. 14, 2012

(54) COOLING POUCH

(75) Inventors: Henry Garnet Wolsey, Haverfordwest (GB); Althea Wolsey, Haverfordwest (GB)

(73) Assignee: Frio UK Ltd., Haverfordwest (GB)

Reexamination Request:
No. 90/010,294, Sep. 24, 2008

Reexamination Certificate for:
Patent No.: 6,067,803
Issued: May 30, 2000
Appl. No.: 09/102,340
Filed: Jun. 22, 1998

Related U.S. Application Data

(63) Continuation-in-part of application No. PCT/GB97/02930, filed on Oct. 23, 1997.

(30) Foreign Application Priority Data

Oct. 23, 1996 (GB) .............................................. 9622047
Apr. 4, 1997 (GB) .............................................. 9706888

(51) Int. Cl.
*F25D 3/08* (2006.01)
*F25D 1/00* (2006.01)
*F25D 1/02* (2006.01)
*F25D 5/02* (2006.01)
*F25D 5/00* (2006.01)
*F25D 3/00* (2006.01)
*A61J 1/14* (2006.01)
*A61J 1/16* (2006.01)

(52) U.S. Cl. ................................ 62/60; 62/457.9; 383/4
(58) Field of Classification Search ........................ None
See application file for complete search history.

(56) References Cited

To view the complete listing of prior art documents cited during the proceeding for Reexamination Control Number 90/010,294, please refer to the USPTO's public Patent Application Information Retrieval (PAIR) system under the Display References tab.

*Primary Examiner* — Cary Wehner

(57) ABSTRACT

A portable flexible cooling pouch for cooling and storing vials containing medication. The pouch comprises opposed web members made of a water permeable material which are connected at the edges thereof. At least one of the web members comprises a plurality of compartments which contain a water-absorbent granular material.

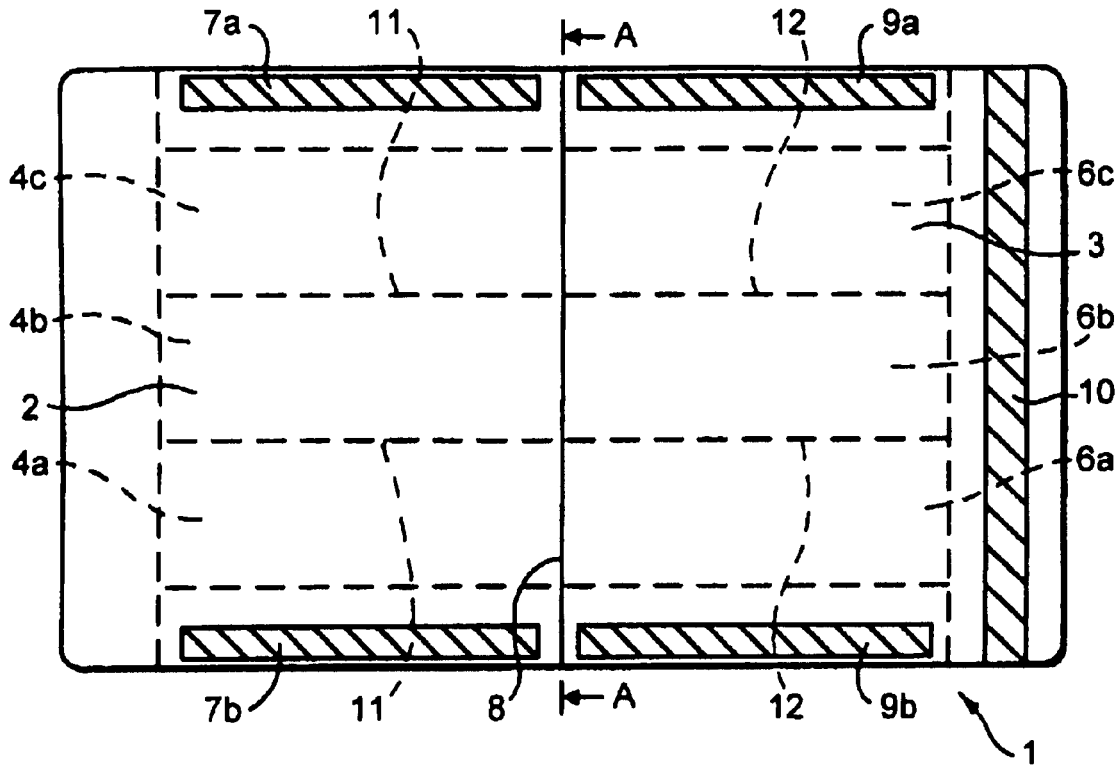

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-32 are cancelled.
Claims 33-57 were not reexamined.

\* \* \* \* \*